United States Patent
Boesen et al.

(10) Patent No.: US 10,045,116 B2
(45) Date of Patent: Aug. 7, 2018

(54) EXPLOSIVE SOUND PRESSURE LEVEL ACTIVE NOISE CANCELLATION UTILIZING COMPLETELY WIRELESS EARPIECES SYSTEM AND METHOD

(71) Applicant: BRAGI GmbH, München (DE)

(72) Inventors: Peter Vincent Boesen, München (DE); Darko Dragicevic, München (DE)

(73) Assignee: BRAGI GmbH, München (DE)

(*) Notice: Subject to any disclaimer, the term of this patent is extended or adjusted under 35 U.S.C. 154(b) by 0 days.

(21) Appl. No.: 15/458,905

(22) Filed: Mar. 14, 2017

(65) Prior Publication Data
US 2017/0263236 A1    Sep. 14, 2017

Related U.S. Application Data

(60) Provisional application No. 62/308,106, filed on Mar. 14, 2016.

(51) Int. Cl.
*G10K 11/16*    (2006.01)
*H04R 1/10*     (2006.01)
(Continued)

(52) U.S. Cl.
CPC .......... *H04R 1/1083* (2013.01); *A61F 11/08* (2013.01); *G10K 11/17835* (2018.01);
(Continued)

(58) Field of Classification Search
CPC .. H04R 1/1083; H04R 1/1016; H04R 1/1041; H04R 2420/07; H04R 2460/01;
(Continued)

(56) References Cited

U.S. PATENT DOCUMENTS 3,934,100 A    1/1976  Harada
4,150,262 A    4/1979  Ono
(Continued)

FOREIGN PATENT DOCUMENTS

CN    204244472 U    4/2015
CN    104683519 A    6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Norman Yu
(74) *Attorney, Agent, or Firm* — Goodhue, Coleman & Owens, P.C.

(57) ABSTRACT

A system includes a first earpiece having an earpiece housing configured to isolate an ambient environment from a tympanic membrane by physically blocking ambient sound, a microphone disposed within the housing and configured to receive a first ambient audio signal from the ambient environment, a processor operatively connected to the microphone wherein the processor is configured to receive the first ambient audio signal from the microphone and determine if the first ambient signal exceeds a threshold sound level, and a speaker operatively connected to the processor. In a first mode of operation the processor determines that the first ambient audio signal exceeds the threshold sound level and processes the first ambient audio signal to modify the first ambient audio signal. In a second mode of operation the processor determines that the first ambient audio signal does not exceed the threshold sound level and reproduces the first ambient audio signal at the speaker.

8 Claims, 5 Drawing Sheets

(51) Int. Cl.
*A61F 11/08* (2006.01)
*G10K 11/178* (2006.01)
*H04R 5/02* (2006.01)
*A61F 11/14* (2006.01)

(52) U.S. Cl.
CPC .............................. *A61F 2011/145* (2013.01);
*G10K 2210/1081* (2013.01); *H04R 1/1016*
(2013.01); *H04R 1/1041* (2013.01); *H04R 2420/07* (2013.01); *H04R 2460/01* (2013.01)

(58) Field of Classification Search
CPC ...... G10K 11/17835; G10K 2210/1081; A61F 11/08; A61F 2011/145
USPC ........ 381/7, 10, 23.1, 300, 309, 311, 26, 56, 381/57, 328, 71.6, 74, 94.5, 94.7, 95, 381/106, 107, 122, 370, 371, 372, 373, 381/374, 375, 376, 380
See application file for complete search history.

(56) References Cited

U.S. PATENT DOCUMENTS

| | | |
|---|---|---|
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| 7,463,902 B2 | 12/2008 | Boesen |
| 7,508,411 B2 | 3/2009 | Boesen |
| 7,825,626 B2 | 11/2010 | Kozisek |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Mullenborn et al. |
| 8,436,780 B2 | 5/2013 | Schantz et al. |
| 8,719,877 B2 | 5/2014 | VonDoenhoff et al. |
| 8,891,800 B1 | 11/2014 | Shaffer |
| 8,994,498 B2 | 3/2015 | Agrafioti et al. |
| 9,013,145 B2 | 4/2015 | Castillo et al. |
| 9,037,125 B1 | 5/2015 | Kadous |
| 9,081,944 B2 | 7/2015 | Camacho et al. |
| 9,510,159 B1 | 11/2016 | Cuddihy et al. |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0258412 A1 | 11/2006 | Liu |
| 2008/0090622 A1 | 4/2008 | Kim et al. |
| 2008/0137873 A1* | 6/2008 | Goldstein ............ H04R 1/1016 381/57 |
| 2008/0146890 A1 | 6/2008 | LeBoeuf et al. |
| 2008/0226094 A1* | 9/2008 | Rutschman ......... H04M 1/6066 381/79 |
| 2008/0254780 A1 | 10/2008 | Kuhl et al. |
| 2009/0017881 A1 | 1/2009 | Madrigal |
| 2009/0073070 A1 | 3/2009 | Rofougaran |
| 2009/0296968 A1 | 12/2009 | Wu et al. |
| 2010/0033313 A1 | 2/2010 | Keady et al. |
| 2010/0203831 A1 | 8/2010 | Muth |
| 2010/0215198 A1* | 8/2010 | Ngia ..................... H04R 1/1016 381/309 |
| 2010/0320961 A1 | 12/2010 | Castillo et al. |
| 2011/0286615 A1 | 11/2011 | Olodort et al. |

(56) References Cited

U.S. PATENT DOCUMENTS

| | | | | |
|---|---|---|---|---|
| 2013/0293723 | A1* | 11/2013 | Benson | G02B 27/017 348/164 |
| 2014/0010378 | A1* | 1/2014 | Voix | H04R 1/1083 381/57 |
| 2014/0122116 | A1 | 5/2014 | Smythe | |
| 2014/0163771 | A1 | 6/2014 | Demeniuk | |
| 2014/0185828 | A1 | 7/2014 | Helbling | |
| 2014/0222462 | A1 | 8/2014 | Shakil et al. | |
| 2014/0270227 | A1 | 9/2014 | Swanson | |
| 2014/0270271 | A1 | 9/2014 | Dehe et al. | |
| 2015/0028996 | A1 | 1/2015 | Agrafioti et al. | |
| 2015/0148989 | A1 | 5/2015 | Cooper et al. | |
| 2015/0245127 | A1 | 8/2015 | Shaffer | |
| 2016/0033280 | A1 | 2/2016 | Moore et al. | |
| 2016/0073189 | A1 | 3/2016 | Lindén et al. | |

FOREIGN PATENT DOCUMENTS

| | | |
|---|---|---|
| CN | 104837094 A | 8/2015 |
| EP | 1017252 A3 | 5/2006 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is On Facebook (2014).
BRAGI Update—Arrival Of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready To Rumble, A Lot To Be Done Over Christmas (Dec. 22, 2014).
BRAGI Update—Memories From April—Update On Progress (Sep. 16, 2014).
BRAGI Update—Memories from May—Update On Progress—Sweet (Oct. 13, 2014).
BRAGI Update—Memories From One Month Before Kickstarter—Update On Progress (Jul. 10, 2014).
BRAGI Update—Memories From The First Month of Kickstarter—Update on Progress (Aug. 1, 2014).
BRAGI Update—Memories From The Second Month of Kickstarter—Update On Progress (Aug. 22, 2014).
BRAGI Update—New People @BRAGI—Prototypes (Jun. 26, 2014).
BRAGI Update—Office Tour, Tour To China, Tour to CES (Dec. 11, 2014).
BRAGI Update—Status On Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
BRAGI Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status On Wireless, Supply, Timeline and Open House@BRAGI(Apr. 1, 2015).
BRAGI Update—Unpacking Video, Reviews On Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health + Mobility Concept for Wellness in Mobility", Fountain Valley, Californa (2017).
Last Push Before The Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for The Dash (Feb. 12, 2014).
Stretchgoal—Windows Phone Support (Feb. 17, 2014).
The Dash—The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).

* cited by examiner

EXPLOSIVE SOUND PRESSURE LEVEL ACTIVE NOISE CANCELLATION UTILIZING COMPLETELY WIRELESS EARPIECES SYSTEM AND METHOD

PRIORITY STATEMENT

This application claims priority to U.S. Provisional Patent Application 62/308,106, filed on Mar. 14, 2016, and entitled Explosive Sound Pressure Level Active Noise Cancellation Utilizing Completely Wireless Earpieces System and Method, hereby incorporated by reference in its entirety.

FIELD OF THE INVENTION

The present invention relates to wearable devices. More particularly, but not exclusively, the present invention relates to earpieces.

BACKGROUND

Hearing loss due to extremely high decibel sound pressure levels (dB SPL) is a common occupational and safety concern. These explosive sounds can damage the stereocilia found in the organ of Corti, causing temporary or even permanent hearing loss. While hearing loss due to short bursts of high dB sound, commonly referred to as a temporary threshold shift, typically only lasts a few minutes, prolonged exposure to high dB sound can create temporary threshold shifts that can last several days. Repeated exposure to explosive high dB sound can cause permanent threshold shifts, resulting in total hearing loss. Clearly workers exposed to such noise are at heightened risk for both short term and long term hearing loss, potentially rendering such workers unable to fulfill their occupational duties. What is needed are methods, systems, and/or devices that minimize or even eliminate the hearing risks such workers face in the fulfillment of their duties.

SUMMARY

It is a primary object, feature, or advantage of the present invention to improve over the state of the art.

It is a further object, feature, or advantage of the present invention to provide an earpiece capable of modulation of an ambient microphone to accommodate for the detection and presence of a suprathreshold dB SPL input.

It is a still further object, feature, or advantage to provide an earpiece configured for activation of a noise cancellation function specific to the suprathreshold dB SPL frequency.

Another object, feature, or advantage is to provide an earpiece configured for shutting off the ambient microphone upon the detection of the suprathreshold dB SPL frequency.

Yet another object, feature, or advantage is to provide an earpiece configured for maintaining the shutdown of the ambient microphone throughout the duration of the offending suprathreshold SPL frequency.

A still further object, feature, or advantage is to provide an earpiece configured for monitoring of the overall ambient environmental noise level to determine safe levels of ambient environmental noise transmission via the speaker system.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by any objects, features, or advantages stated herein.

In one implementation, a system includes an earpiece configured to isolate an ambient environment within a tympanic membrane in an ear canal. The system also includes a microphone disposed within the earpiece and configured to receive at least one ambient signal, a processor operatively connected to the microphone and configured to receive the at least one ambient signal and determine if the sound level of the ambient signal is higher than a threshold sound level, a speaker proximate the tympanic membrane and operatively connected to the processor wherein the speaker is configured to reproduce the at least one ambient signal if its sound level is not higher than or equal to the threshold sound level, and at least one power source such as a battery operatively connected to the microphone, the processor, and the speaker.

One or more of the following features may be included. The earpiece of the system may comprise an earpiece housing. In addition, the earpiece may consist of a left earpiece and a right earpiece, be composed of a material with low thermal or electrical conductivity, and may further comprise at least one additional microphone. Also, the maximum sound level of the system may be programmed by a user. In addition, the microphone may be configured to detect both air conduction vibrations and bone conduction vibrations.

The system may also have the processor configured to combine the at least one ambient signal with a second signal to create a combined signal if the sound level of the ambient signal is higher than or equal to the threshold sound level. The second signal may also be a noise cancellation signal. In addition, the system may include the processor configured to attenuate the ambient signal if the sound level of the ambient signal is higher than or equal to the threshold sound level. The system may also include the processor configured to instruct the microphone to cease reception and the speaker to cease transmission if the sound level of the ambient signal is higher than or equal to the threshold sound level.

In another implementation, a method of modulating sound within an earpiece includes receiving, via a microphone, at least one ambient signal and transmitting the at least one ambient signal to a processor. The processor compares the sound level of the at least one ambient signal with the maximum sound level and transmits the at least one ambient signal to a speaker if the sound level of the at least one ambient signal is lower than the maximum sound level. The speaker then transmits the at least one ambient signal to a tympanic membrane within an ear canal of a user.

One or more of the following features may be included. The earpiece may include an extra microphone which may be used to detect an ambient sound level. Also, the microphone or the extra microphone may be used to continuously monitor an ambient sound level and the maximum sound level may be programmable by a user.

The method may also include the cessation of reception by the microphone if the ambient sound level is equal to or higher than the maximum sound level and instructing the processor to, in lieu of not transmitting the at least one ambient signal to a speaker if the sound level of the at least one ambient signal is equal to or higher than the maximum sound level, combine the at least one ambient signal with a second signal generated by the processor to produce a combined signal if the processor received the at least one ambient signal from the microphone, wherein the combined signal has a sound level lower than the maximum sound level. The combined signal may then be transmitted to the speaker and then transmitted to the tympanic membrane of the user. If the ambient sound level falls below the maximum sound level, the microphone may resume reception of the at least one ambient signal. The processor may also attenuate the at least one ambient signal in lieu of creating the combined signal. The processor may also instruct the speaker to cease transmission if the ambient sound level is equal to or higher than the maximum sound level, and then resume transmission when the ambient sound level drops below the maximum sound level.

According to another aspect, a system includes a first earpiece having an earpiece housing configured to isolate an ambient environment from a tympanic membrane by physically blocking ambient sound, a microphone disposed within the housing and configured to receive a first ambient audio signal from the ambient environment, a processor operatively connected to the microphone wherein the processor is configured to receive the first ambient audio signal from the microphone and determine if the first ambient signal exceeds a threshold sound level, and a speaker operatively connected to the processor. In a first mode of operation the processor determines that the first ambient audio signal exceeds the threshold sound level and processes the first ambient audio signal to modify the first ambient audio signal. In a second mode of operation the processor determines that the first ambient audio signal does not exceed the threshold sound level and reproduces the first ambient audio signal at the speaker.

The first earpiece may further include a transceiver disposed within the earpiece housing for operative communication with a second earpiece, the second earpiece having a microphone, a speaker, and a transceiver. The second earpiece may communicate a second ambient audio signal from the microphone of the second earpiece through the transceiver of the second ear piece, and wherein the transceiver of the first ear piece receives the second ambient audio signal and wherein in the first mode of operation the processor further processes the second ambient audio signal to modify the second ambient audio signal and provide a processed second ambient audio signal and then communicate the processed second ambient signal to the second ear piece and reproduces the processed second ambient signal at the speaker of the second earpiece.

The transceiver of the first earpiece may be a near field magnetic induction (NFMI) transceiver and the transceiver of the second earpiece may be an NFMI transceiver. In the first mode of operation the processor may determine that the first ambient audio signal exceeds the threshold sound level and processes the first ambient audio signal to modify the first ambient audio signal by reducing a signal level of the first ambient audio signal. The processing may also or alternatively modify the first ambient audio signal by filtering frequencies from the first, add a noise cancellation signal to the first ambient audio signal, or otherwise process.

In the first mode of operation the processor may further communicate through the transceiver that the first ambient audio signal exceeds the threshold sound level. In a third mode of operation the processor may receive from the transceiver a communication that a second ambient audio signal from the microphone of the second earpiece exceeds the threshold sound level and processes the first ambient audio signal to modify the first ambient audio signal. The threshold sound level may be a user adjustable setting.

DETAILED DESCRIPTION

A system and method is provided to protect the user's ears from the damaging effects of high level dB SPL noise exposures using a device designed to utilize the external microphone or microphones of an earpiece worn at the external canal and well fitting. In addition to closure of the microphone when a loud noise is detected at a level above a preset threshold, the system would shut off the microphone and/or otherwise prevent transmission of the sound through the device speaker. In addition to this, transient anti-sound may also be delivered to the speaker so that an additive effect of active noise cancellation to the passive noise cancellation already provided by the fit of the external auditory canal device. Such cancellation may provide transient and reproducible levels of protection to the user. After the suprathreshold level of sound input has passed, the system may respond by opening up the auditory channel once again for transmission of ambient environmental sounds, albeit at lower and non-damaging levels of dB SPL inputs.

Figure 1:
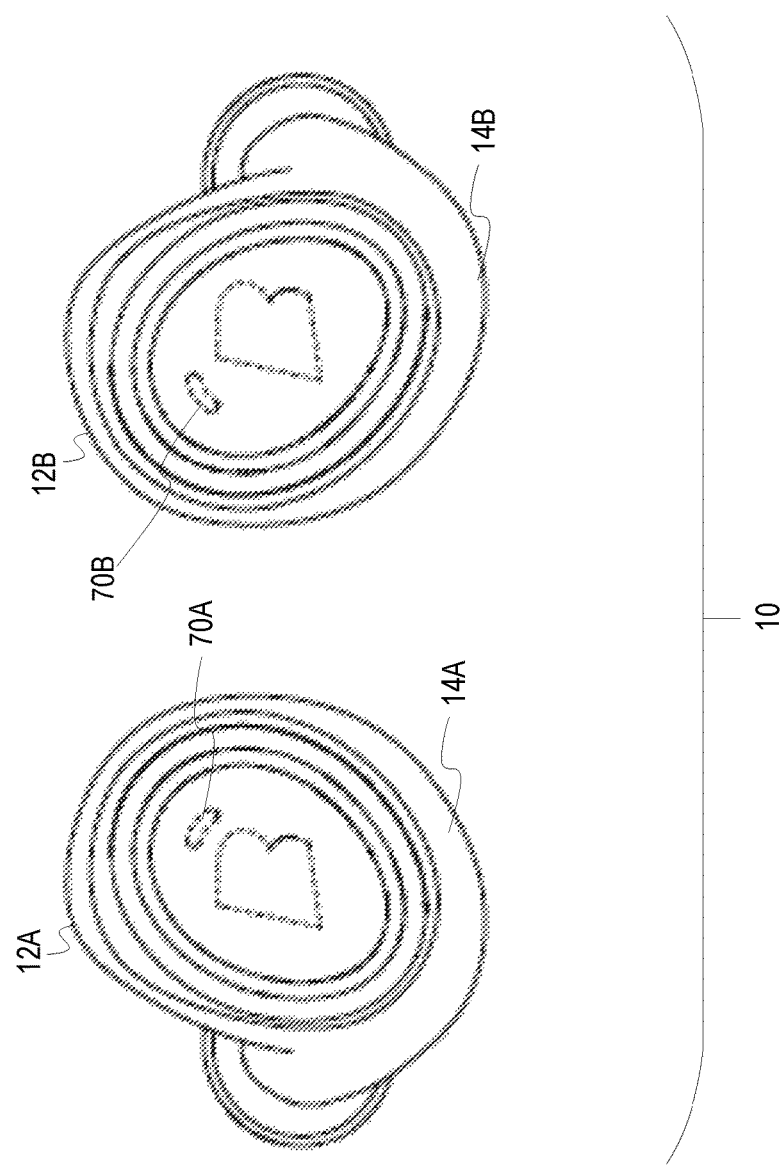
FIG. 1 illustrates one example of a set of earpieces.

FIG. 1 illustrates one example of a set of earpieces 10 which include a left earpiece 12A and a right earpiece 12B. The left earpiece 12A has a housing 14A and the right earpiece 12B has a housing 14B. An externally facing microphone 70A is shown on the left earpiece and externally facing microphone 70B is shown on the right earpiece.

Figure 2:
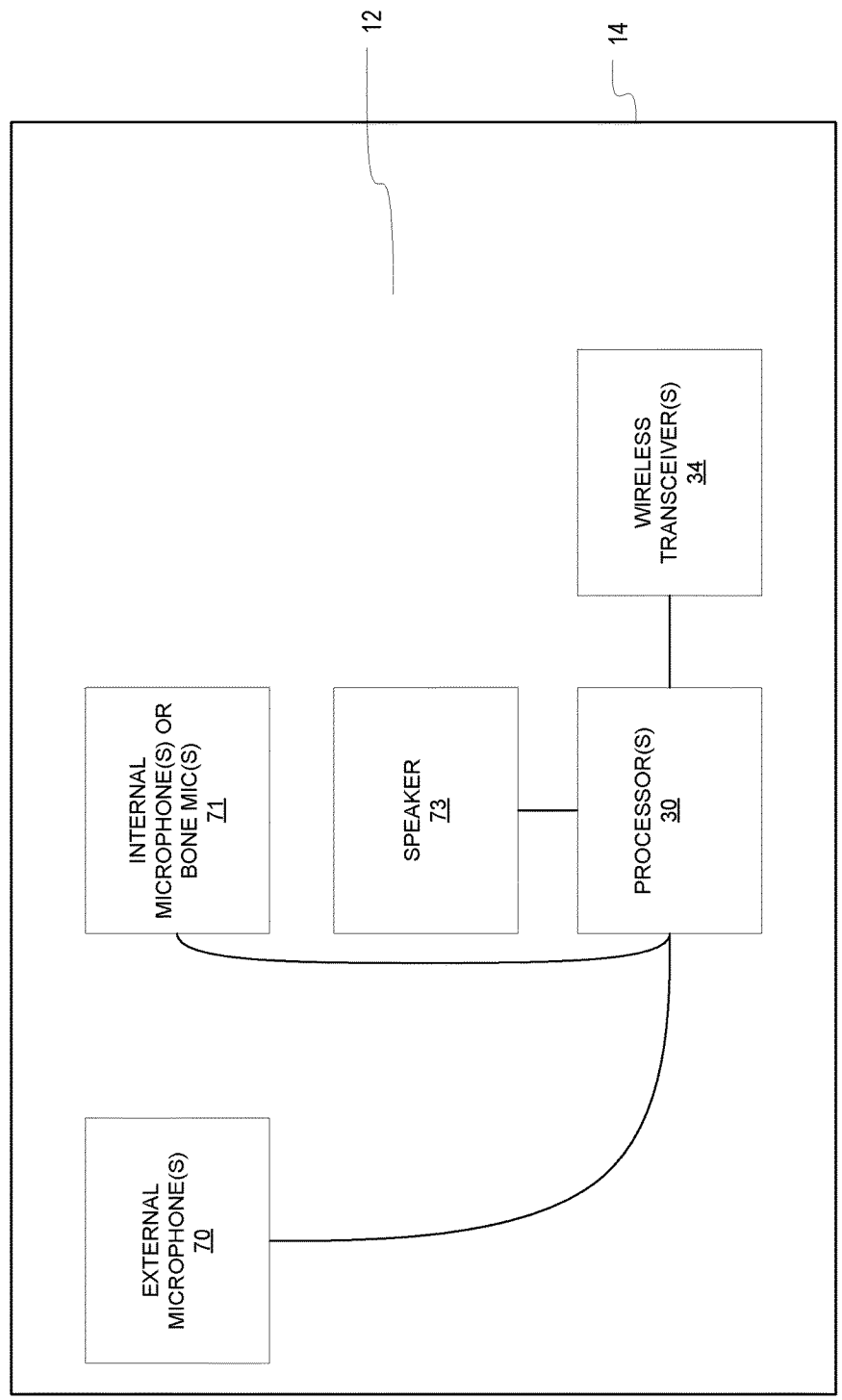
FIG. 2 is a block diagram of one example of an earpiece.

FIG. 2 illustrates a block diagram of one example of an earpiece 12 which may be a left earpiece or a right earpiece. The earpiece 12 has a housing 14. One or more processors 30 are shown disposed within the housing 14. The one or more processors may include one or more digital signal processors, mixed signal processors, micro-processors or other types of processor. Where the term "processor" is used herein, it is to be understood that it may refer to a single processor or multiple processors. One or more external microphones 70 are operatively connected to the processor 30. Similarly, one or more internal microphone 71 are operatively connected to the processor 30. A speaker 73 is also shown which is operatively connected the processor 30. A wireless transceiver 34 may be operatively connected to the processor 30.

Figure 3:
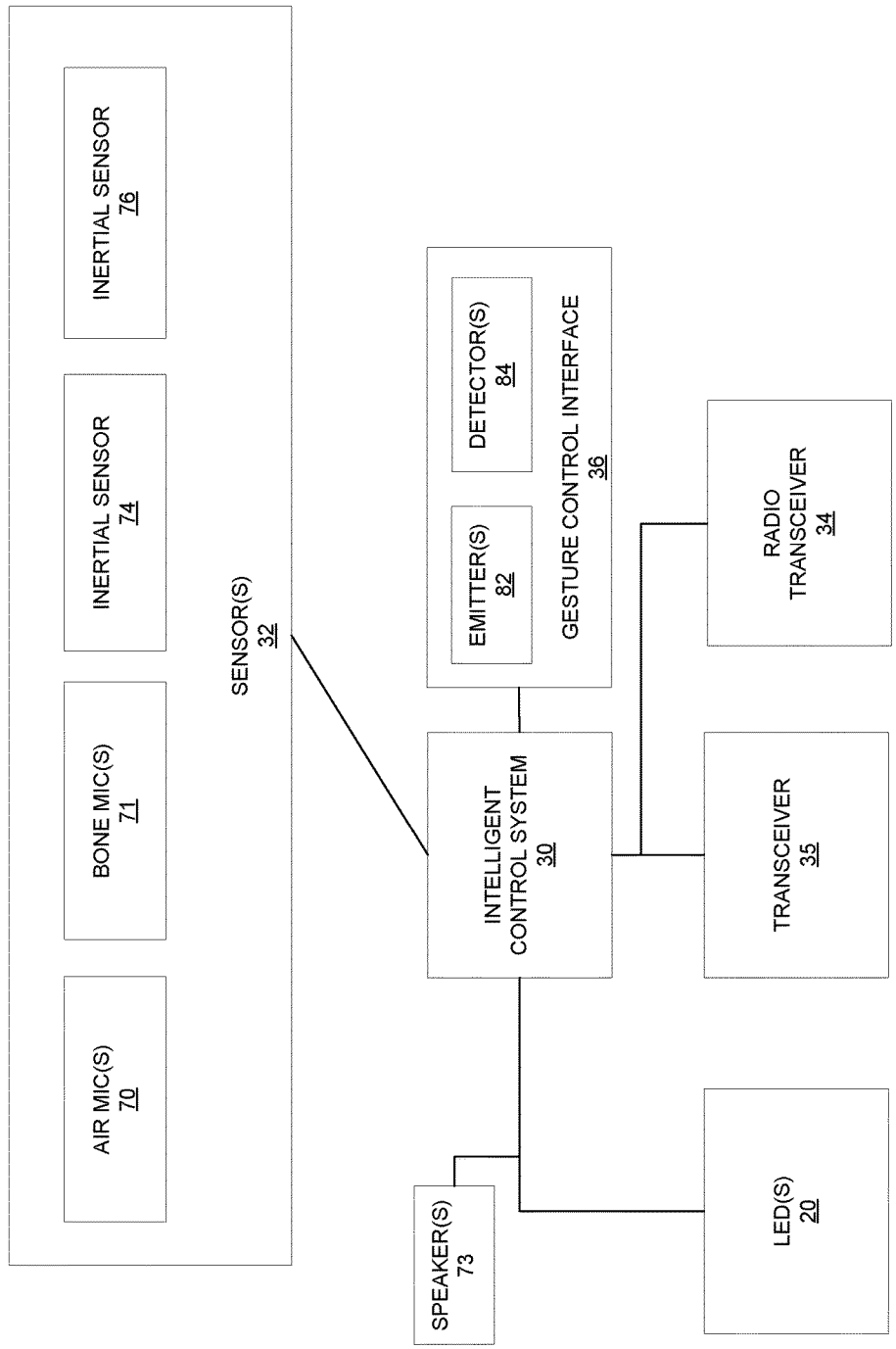
FIG. 3 is another block diagram of an earpiece.

FIG. 3 is a block diagram illustrating an earpiece. The earpiece may include one or more sensors 32. The sensors may include one or more air microphones 70, one or more bone microphones 71, and one or more inertial sensors 74, 76. Each of the one or more sensors 32 is operatively connected to an intelligent control system 30. The intelligent control system 30 may also be operatively connected to a gesture control interface 36 which may include one or more emitters 82 and one or more detectors 84. The gesture control interface 36 allows a user to interact with the earpiece through gestures or motions which are detected by the gesture control interface and interpreted by the intelligent control system 30. One or more speakers 72 is operatively connected to the intelligent control system 30. One or more light emitting diodes 20 are operatively connected to the intelligent control system 30 that may be used to provide visual feedback indicative of earpiece functionality or status. A radio transceiver 34 is shown as well as a second transceiver 35 which may be a near field magnetic induction (NFMI) transceiver or other type of transceiver. The second transceiver 35 may be used for communicating with another earpiece. It is to be understood that a system or set of earpieces having both a left ear piece and a right earpiece may each have all of the functionality shown in FIG. 3. However, it is to also be understood that one of the earpieces may have a subset of the functionality. For example, digital signal processing may be performed entirely or predominantly with one earpiece with audio signals from the other earpiece being communicated to that earpiece through the transceiver 35 for processing.

Figure 4:
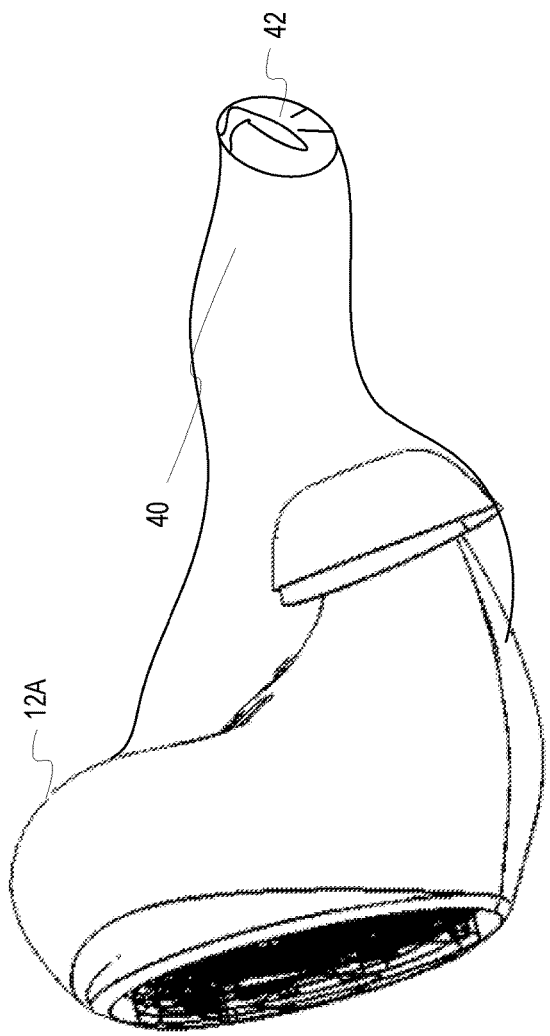
FIG. 4 illustrates an earpiece fitted to an external auditory canal of an individual.

FIG. 4 illustrated one example of an earpiece 12A positioned within an external auditory canal 40 of a person. Sound emitted from the earpiece 12A may be transmitted or directed inwardly towards a tympanic membrane 42 of a user. In addition, note that the position of the earpiece 12A within the external auditory canal 40 of the user provides for isolating sound from an ambient environment from the tympanic membrane 42. Thus, the only or substantially only sound that the tympanic membrane 16 receives is sound received from the earpiece 12A. The ear piece as shown may be a small device which fits comfortably within the external auditory canal but may also be a one-piece headset that covers both ears. The earpiece 12A is preferably made from a material with low thermal conductivity so that the earpiece 12A is comfortable to wear. In addition, the earpiece may be insulated.

Figure 5:
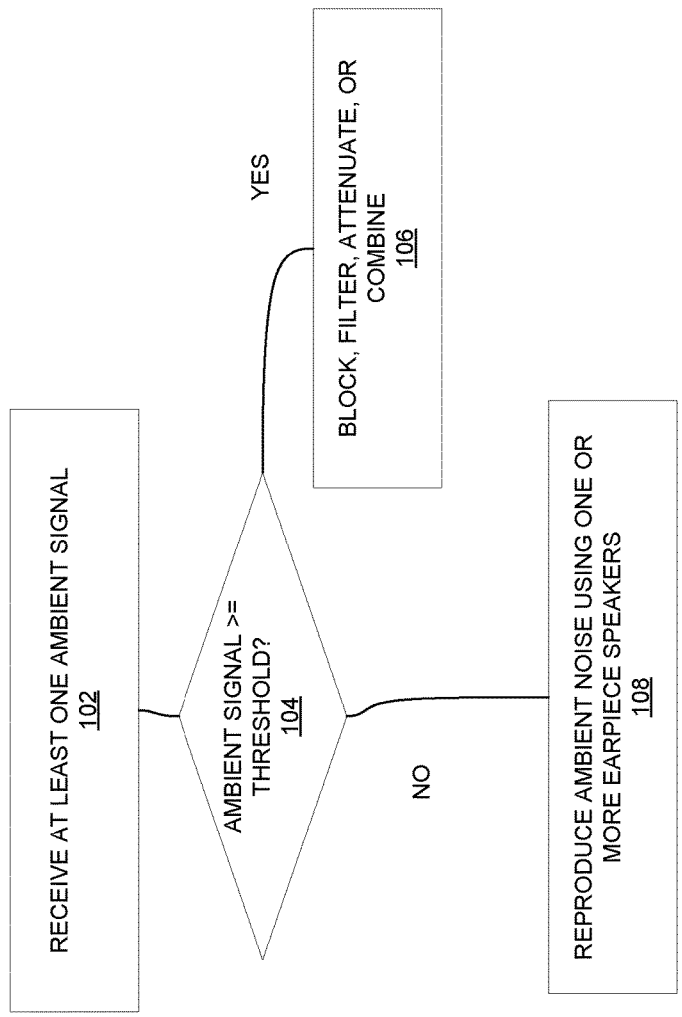
FIG. 5 is one example of a flow diagram.

FIG. 5 is a block diagram illustrating one example of a methodology. In step 102 at least one ambient signal is received from one or more microphones or other audio inputs of an earpiece. In step 104 a determination is made as to whether the ambient signal is greater than or equal to a threshold. The threshold may be associated with a decibel level which may damage the ear or result in temporary or permanent hearing loss such as by causing temporary or permanent threshold shifts. If in step 104 a determination is made that the ambient signal(s) are greater than a threshold, then in step 106 the ambient signal may be blocked, filtered, attenuated, or combined with another signal such as an ambient sound cancelling signal. When an ambient signal is blocked, this can be accomplished in various ways. For example, the speaker may simply be turned off for the duration that the ambient signal exceeds the threshold. Alternatively, the ambient signal may be attenuated so that a lower amplitude version of the ambient signal is reproduced at the speaker(s) of the earpiece. The processor may also perform more sophisticated processing. For example, the particular sound within the ambient signal may be filtered from the remainder of the ambient signal. Frequencies of the sound may be filtered out. The remainder of the ambient signal may be reproduced either without the particular threshold exceeding sound present or combined with an attenuated version of the otherwise threshold exceeding sound present. The same effect may be generated by creating a combined signal of the original ambient signal and another signal which cancels all or a portion of the particular threshold exceeding sound. Thus, in a first mode of operation the processor determines that the first ambient audio signal exceeds the threshold sound level and processes the first ambient audio signal to modify the first ambient audio signal. In a second mode of operation the processor determines that the first ambient audio signal does not exceed the threshold sound level and reproduces the first ambient audio signal at the speaker.

It is also to be understood that in some embodiments a wireless earpiece is in operative communication with another wireless earpiece. Where two earpieces are present, one earpiece may perform all of the audio processing with its processor and thus when the processor of the earpiece determines that either the ambient audio from the left earpiece or the ambient audio from the right earpiece exceeds the threshold, the ambient audio is reproduced or else shutoff either by disabling the microphone and/or speaker. Where two earpieces are present and each earpiece performs its own audio processing, a signal may be communicated from one earpiece to the other earpiece to indicate that the threshold has been met. Thus, the earpiece receiving the signal or communication indicating that the threshold has been met for the other earpiece may then perform the same processing. Thus, the two earpieces may process ambient audio in the same way so that the user hears the same experience in both ears as opposed to having each earpiece work independently without coordination between the two. This processing based on what is determined from another earpiece may be considered a third mode of operation.

The first earpiece may further include a transceiver disposed within the earpiece housing for operative communication with a second earpiece, the second earpiece having a microphone, a speaker, and a transceiver. The second earpiece may communicate a second ambient audio signal from the microphone of the second earpiece through the transceiver of the second ear piece, and wherein the transceiver of the first ear piece receives the second ambient audio signal and wherein in the first mode of operation the processor further processes the second ambient audio signal to modify the second ambient audio signal and provide a processed second ambient audio signal and then communicate the processed second ambient signal to the second ear piece and reproduces the processed second ambient signal at the speaker of the second earpiece.

Thus, a method of modulating sound within an earpiece includes receiving, via a microphone, at least one ambient signal and transmitting, via the microphone, the at least one ambient signal to a processor. The method further includes comparing, via the processor, a sound level or other property of the at least one ambient signal and a maximum sound level or other sound property with a threshold level. The method further includes communicating, via the processor, the at least one ambient signal to a speaker if the sound level of the at least one ambient signal is lower than the threshold or maximum sound level, and transmitting, via the speaker, the at least one ambient signal to a tympanic membrane.

The threshold or maximum sound level may be determined in various ways. For, example, it may be a universal maximum sound level. Alternatively, it may be programmed into an individual earpiece for a particular individual after an audiometric analysis performed either by the earpiece itself (alone or in combination with one or more computing devices), or by an audiologist or other appropriate personnel. Where the setting is a user setting, the user may communicate with one or both earpieces in various ways. This may include through voice control, through use of gestural commands, through settings on a connected device such as a mobile device, or otherwise.

Therefore, various apparatus, system, and methods have been shown and described herein. Although specific embodiments have been shown, the present invention contemplates numerous variations, options, and alternatives.

What is claimed is:

1. A system comprising:
  a first earpiece having an earpiece housing configured to isolate an ambient environment from a tympanic membrane by physically blocking ambient sound, wherein the first earpiece further comprises:

a microphone disposed within the housing and configured to receive a first ambient audio signal from the ambient environment, a transceiver disposed within the earpiece housing for operative communication with a second earpiece, a processor operatively connected to the microphone wherein the processor is configured to receive the first ambient audio signal from the microphone and determine if the first ambient signal exceeds a threshold sound level, and a speaker operatively connected to the processor;

wherein in a first mode of operation the processor determines that the first ambient audio signal exceeds the threshold sound level and processes the first ambient audio signal to modify the first ambient audio signal;

wherein a second mode of operation the processor determines that the first ambient audio signal does not exceed the threshold sound level and reproduces the first ambient audio signal at the speaker;

the second earpiece having a microphone, a speaker, and a transceiver; and wherein the second earpiece communicates a second ambient audio signal from the microphone of the second earpiece through the transceiver of the second ear piece, and wherein the transceiver of the first ear piece receives the second ambient audio signal and wherein in the first mode of operation the processor further processes the second ambient audio signal to modify the second ambient audio signal and provide a processed second ambient audio signal and then communicate the processed second ambient signal to the second ear piece and reproduce the processed second ambient signal at the speaker of the second earpiece.

2. The system of claim 1 wherein the transceiver of the first earpiece is a near field magnetic induction (NFMI) transceiver and wherein the transceiver of the second earpiece is a NFMI transceiver.

3. The system of claim 1 wherein in the first mode of operation the processor determines that the first ambient audio signal exceeds the threshold sound level and processes the first ambient audio signal to modify the first ambient audio signal by reducing a signal level of the first ambient audio signal.

4. The system of claim 1 wherein in the first mode of operation the processor determines that the first ambient audio signal exceeds the threshold sound level and processes the first ambient audio signal to modify the first ambient audio signal by filtering frequencies from the first ambient audio signal.

5. The system of claim 1 wherein in the first mode of operation the processor determines that the first ambient audio signal exceeds the threshold sound level and processes the first ambient audio signal to modify the first ambient audio signal by adding a noise cancellation signal to the first ambient audio signal.

6. The system of claim 1 wherein in the first mode of operation the processor further communicates through the transceiver to the second earpiece that the first ambient audio signal exceeds the threshold sound level.

7. The system of claim 1 wherein in a third mode of operation the processor receives from the transceiver of the first earpiece a communication that a second ambient audio signal from the microphone of the second earpiece exceeds the threshold sound level and processes the first ambient audio signal to modify the first ambient audio signal.

8. The system of claim 1 wherein the threshold sound level is a user adjustable setting.

\* \* \* \* \*